(12) United States Patent
Olson et al.

(10) Patent No.: US 6,608,883 B2
(45) Date of Patent: Aug. 19, 2003

(54) AUTOMATED SAMPLE HANDLING FOR X-RAY CRYSTALLOGRAPHY

(75) Inventors: Jeffrey A. Olson, Libertyville, IL (US); Ronald B. Jones, Mundelein, IL (US); Vicki L. Nienaber, Gurnee, IL (US); Steven W. Muchmore, Libertyville, IL (US); Jeffrey Y. Pan, Lake Forest, IL (US); Jonathan Greer, Chicago, IL (US)

(73) Assignee: Abbott Laboratories, Abbott Park, IL (US)

( * ) Notice: Subject to any disclaimer, the term of this patent is extended or adjusted under 35 U.S.C. 154(b) by 0 days.

(21) Appl. No.: 10/144,277

(22) Filed: May 10, 2002

(65) Prior Publication Data

US 2002/0126802 A1 Sep. 12, 2002

Related U.S. Application Data

(62) Division of application No. 09/372,134, filed on Aug. 11, 1999, now Pat. No. 6,404,849.

(51) Int. Cl.[7] .............................................. G01N 23/20
(52) U.S. Cl. ........................................ 378/79; 378/208
(58) Field of Search ..................... 378/79, 208; 250/328

(56) References Cited

U.S. PATENT DOCUMENTS

| 4,641,329 A |   | 2/1987 | Green et al. ................... 378/79 |
| 4,770,593 A | * | 9/1988 | Anderson .................... 414/331 |
| 5,359,640 A |   | 10/1994 | Fink et al. ...................... 378/79 |
| 5,737,385 A |   | 4/1998 | Prevey et al. .................. 378/71 |
| 5,964,095 A | * | 10/1999 | Coelho et al. .................. 62/62 |
| 6,064,717 A |   | 5/2000 | Ortega et al. .................. 378/71 |
| 6,301,330 B1 | * | 10/2001 | Kurtz et al. .................... 378/71 |
| 6,408,047 B1 | * | 6/2002 | Kitagawa et al. ............. 378/79 |

FOREIGN PATENT DOCUMENTS

| JP | 09033457 | 2/1997 |
| WO | WO 97/20972 | 6/1997 |

OTHER PUBLICATIONS

E. Garman, et al., Macromolecular Cryocrystallography, Journal of Applied Crystallography, vol. 30 (1997), pp. 211–237.

Hampton Research, Crystallization Research Tool, vol. 9, No. 1, 1999, pp. 50–56.

Kirk–Othmer Encyclopedia of Chemical Technology, 4th Edition, vol.25, pp. 742–760.

* cited by examiner

Primary Examiner—Drew A. Dunn
Assistant Examiner—Jurie Yun
(74) Attorney, Agent, or Firm—David L. Weinstein

(57) ABSTRACT

Method for mounting a sample comprising a crystal for X-ray crystallographic analysis, a method for aligning a sample comprising a crystal for X-ray crystallographic analysis, which sample is mounted on a positioning device, and a method for determining the structure of a sample containing a crystal by means of X-ray crystallography. The method includes activating a robot so that the tool retrieves the crystal holder, receives a sufficient amount of a fluid to maintain the crystal in the crystal holder at a temperature not in excess of about 160 degrees K, transfers the retrieved crystal holder to a positioning device, and mounts the transferred crystal holder on the positioning device, whereby the crystal in the retrieved crystal holder is maintained at a temperature not in excess of about 160 degrees K.

6 Claims, 17 Drawing Sheets

AUTOMATED SAMPLE HANDLING FOR X-RAY CRYSTALLOGRAPHY

This application is a division of U.S. Ser. No. 09/372,134, filed Aug. 11, 1999 now U.S. Pat. No. 6,404,849.

BACKGROUND OF THE INVENTION

1. Field of the Invention

This invention relates to X-ray crystallography, and, in particular, to methods and apparatus for mounting and aligning of samples for X-ray crystallographic analysis.

2. Discussion of the Art

X-ray crystallography is an established, well-studied technique for providing a three-dimensional representation of the appearance of a molecule in a crystal. Scientists have employed X-ray crystallography to determine the crystal structures of many molecules.

In order to perform an X-ray crystallographic analysis, a sample of the crystal must be mounted onto a positioning device, then carefully aligned so that the entire crystal is within the diameter of the X-ray beam, and X-ray diffraction data collected at a number of rotational angles. Because the typical sizes of crystals and the diameter of the X-ray beam are in the range of 100 to 400 micrometers, the alignment requires a high degree of precision. In addition, to ensure the integrity of crystals, the crystals must be stored under liquid nitrogen and maintained at temperatures near that of liquid nitrogenduring the entire mounting, aligning, and data collecting processes. Currently, mounting and aligning of samples is performed manually.

A typical X-ray crystallography apparatus comprises an X-ray generator, a detector, and a rotating spindle onto which a finely adjustable head of the positioning device is mounted. Raw diffraction data collected by the detector are input into a computer for processing. The head of the positioning device allows minute adjustments in two axes that are perpendicular to one another and to the axis of the spindle. Some heads of positioning devices also allow for angular input into a computer for processing. The head of the positioning device allows minute adjustments in two axes that are perpendicular to one another and to the axis of the spindle. Some heads of positioning devices also allow for angular adjustments in one or more axes. A third axis of adjustment is provided by translation of the rotating spindle in a direction that is orthogonal to the two axes of the head of the positioning device. The sample mount position of the head of the positioning device is positioned so that when mounted, the sample is near the centerline of the X-ray beam. A CCD camera is mounted so that a magnified image of the mounted sample can be displayed on a video monitor. Cross-hairs on the video display indicate the desired position of the sample, corresponding to the intersection of the center of the X-ray beam with the axis of the spindle. In order to maintain the sample at a sufficiently low temperature once it is mounted, a stream of cold nitrogen gas is directed at the sample mount position.

The procedure for mounting and aligning a sample manually is described below. An operator places a sample into a small canister of liquid nitrogen and then maneuvers the canister near to the sample mount position on the head of the positioning device. As quickly as possible, the operator withdraws the sample and mounts it onto the head of the positioning device. Using the video image on the monitor, the operator turns adjustment screws controlling the "X", "Y", and "Z" axes until the sample is centered within the X-ray beam and spindle axes (as indicated by the cross-hairs on the video display). After the sample has been centered, analysis of the sample by X-ray diffraction is begun. The procedure is described in detail in Garman, et al., "Macromolecular Cryocrystallography", J. Appl. Cryst. (1997) 30, 211–237 (hereinafter "Garman et al."), incorporated herein by reference.

According to Garman et al., there are numerous problems involved in manual procedures for X-ray-diffraction data collection from macromolecular crystals at cryogenic temperatures. According to Garman, prerequisites for starting a cryogenic data collection are a reliable cryostat, the ability to maintain an ice-free environment, some crystal-mounting equipment, a sufficient number of crystals, and some manual dexterity for smooth and rapid operation on the part of the operator. An important part of a cryocrystallographic data collection is the method of crystal mounting and the hardware associated with it. Macromolecular crystals require special treatment compared to crystals of small molecules, because macromolecular crystals have a liquid content ranging from approximately 5 to 70%. The current most widely used technique is the loop method, wherein a loop is used to suspend a crystal by surface tension in a thin film of cryoprotected buffer. The first loops were made of gold-plated tungsten wire. These metal loops were replaced by loops made from various fine (10–50 $\mu$m diameter) fibers that do not absorb and scatter X-rays to the same extent as metal, such as hair, fibers of glass, nylon, rayon, fly-fishing threads, unwaxed dental floss, cotton, surgical thread and mohair wool.

There are several ways of connecting the loop-supporting pin to the head of the positioning device. Two widely used methods are insertion of a pin directly into the hole in the head of the positioning device and attachment of a magnet to the head of the positioning device, to which a magnetic pin-holder is attracted and rigidly held.

Evaporation from the film suspended in the loop is very rapid because of its large surface-to-volume ratio. Therefore, one of the most critical parameters in a cryocrystallographic experiment is the time between picking up the crystal and flash cooling it. This time should be as short as possible, ideally less than one second, otherwise the crystal can dehydrate or components of the buffer can precipitate. According to Garman et al., all manipulations and motions should be practised on several dry runs with nothing in the loop, to ensure smooth and rapid operation later on. No time should be wasted in viewing the crystal within the loop, since flash cooling an empty loop is less harmful than losing crystals before cooling by stopping to check whether they really are in the loop.

For most protein crystals, flash cooling in a gas stream is perfectly adequate and represents the safest and simplest option. From a practical standpoint, for gas-stream flash cooling it is helpful at first to have a second operator present who can divert the cold gas stream by holding a piece of card over it as soon as the "fisher" signals that the crystal is caught. Once the crystal is positioned, the card is then swiftly whipped away ensuring rapid and reproducible cooling. Experienced cryocrystallographers tend to divert the cold gas stream themselves or do not divert it at all while placing the crystal on the head of the positioning device, success depending on the quickness and certainty of their action.

The most common difficulty experienced by experimenters starting to use cryotechniques is ice around, near, on, and/or in the crystal. There are several reasons for ice forming around the crystal. The end of the cryonozzle may be positioned too far from the crystal: ideally it should be as close as possible since the temperature profile of the cold nitrogen stream is very sharp (the temperature rises from 100° K. to room temperature over a few millimeters for most open-flow systems). In addition, further away from the nozzle the gas stream becomes dissipated and is thus more susceptible to the effects of turbulence and drafts. If placing the cryonozzle near the crystal results in a shadow on the X-ray detector, thought should be given to changing the angle of approach of the stream. If this proves impossible, the shadow can be masked out during data processing.

A question that often arises concerns the optimum angle of incidence of the cold stream on the crystal. This is not an important factor in a draft-free and carefully monitored experiment. However, most cold streams operate better with the gas flowing downwards. Also, experimental constraints must be taken into account. For instance, for crystal storage enough space must be available to allow cryovial access.

In general, a major reason for ice formation is turbulent flow at the boundaries between the cold gas and warm coaxial stream and between the latter and warm wet air in the room. To prevent this and to allow the desired laminar flow, the flow velocities of the cold and the warm dry gases must be matched. To match the flows, the relative areas of the two gas streams can be calculated and the rates scaled accordingly.

Many classes of biological molecules can be studied by X-ray crystallography, including, but not limited to, proteins, DNA, RNA, and viruses. Scientists have reported the crystal structures of molecules that carry ligands within their receptors, i. e., ligand-receptor complexes.

Given a representation of a target molecule or ligand-receptor complex, scientists can search for pockets or receptors where biological activity can take place. Then scientists can experimentally or computationally design high-affinity ligands (or drugs) for the receptors. Computational methods have alternatively been used to screen for the binding of small molecules. However, these previous attempts have met with limited success. Several problems plague ligand design by computational methods. Computational methods are based on estimates rather than on exact determinations of the binding energies, and rely on simple calculations when compared with the complex interactions that exist within a biomolecule. Moreover, computational models require experimental confirmation, which often expose the models as false positives that do not work on the actual target.

It has recently been discovered that X-ray crystallography can be used to screen compounds that are not known ligands of a target biomolecule for their ability to bind the target. The method comprises the steps of obtaining a crystal of a target biomolecule, exposing the target to one or more test samples that are potential ligands of the target, and determining whether a ligand/biomolecule complex is formed. The target is exposed to potential ligands by various methods, including but not limited to, soaking a crystal in a solution of one or more potential ligands or co-crystallizing a biomolecule in the presence of one or more potential ligands. Structural information from the ligand-receptor complexes found can be used to design new ligands that bind tighter, bind more specifically, have better biological activity or have better safety profiles than known ligands.

According to this novel method, ligands for a target molecule having a crystalline form are identified by exposing a library of small molecules, either singly or in mixtures, to the target (e. g., protein, nucleic acid, etc.). Then, one obtains crystallographic data to compare the electron density map of the putative target-ligand complex with the electron density map of the target biomolecule. The electron density map simultaneously provides direct evidence of ligand binding, identification of the bound ligand, and the detailed three-dimensional structure of the ligand-target complex. Binding may also be monitored by changes in individual reflections within the crystallographic diffraction pattern which are known to be sensitive to ligand binding at the active site. This could serve as a pre-screen but would not be the primary method of choice because it provides less detailed structural information.

By observing changes in the level of ligand electron density or the intensity of certain reflections in the diffraction pattern as a function of ligand concentration either added to the crystal or in co-crystallization, one may also determine the binding affinities of ligands for biomolecules. Binding affinities may also be obtained by competition experiments. Here, the new compound(s) are soaked or co-crystallized with one of a series of diversely-shaped ligands of known binding affinity. If the known ligand appears in the electron density map, the unknown ligands are weaker binders. However, if one of the new compounds is found to compete for the site, it would be the tighter binder. By varying the concentration or identity of the known ligand, a binding constant for the hit may be estimated.

Screening requires exposing a target molecule to thousands of compounds singly or in mixtures. Screening by means of X-ray crystallography requires examining many crystals, which in turn can involve many days of operating 24 hour per day. Such thorough screening can only be accomplished by means of an automated system for mounting crystals onto the X-ray instrument and for aligning the crystals to the X-ray beam.

The use of cryogenic techniques brings great advantages to the crystallographer. One advantage is that the great reduction in radiation damage to crystals at cryogenic temperatures gives the crystallographer effectively infinite crystal lifetimes on an in-house source and vastly extended lifetimes on a synchrotron. Another advantage of cryogenic data collection is that the crystal mounting methods used are mechanically gentler and involve less sample handling. A third advantage of the technique is the facility for in-house screening of flash-cooled crystals and the possibility of storing and transporting them.

The major problem with the use of cryogenic techniques is the high expense of trained operators to mount the samples and collect the data. Therefore, it would be desirable to develop a method for collecting X-ray crystallographic data automatically, without the necessity of a trained operator being present.

Synchrotron X-radiation has become a very common source of X-rays for examining crystals of all types of molecules, small and macromolecular. Because of the particularly intense X-rays available at a synchrotron, cryocooling of samples is usually desirable and often necessary. Although the intense X-rays result in a large reduction in data collection times, often as low as minutes, safety issues complicate sample loading so that the steps of crystal mounting and alignment to the X-ray beam often take as long as or even longer than the data collection step itself. The duration of these mounting and alignment steps results in a significant lowering of efficiency in the use of synchrotron beamlines, which are in great demand and expensive to construct and operate. An automated device for mounting crystal samples onto the X-ray instrument and for accurately aligning the crystal samples to the X-ray beam would significantly reduce the time required for sample loading and greatly accelerate the process of examining a great number of samples. Thus, an automated device would achieve a significant increase in efficiency in the use of synchrotron beamlines.

SUMMARY OF THE INVENTION

In one aspect, this invention provides a method for mounting a sample comprising a crystal for X-ray crystallographic analysis, which method comprises the steps of:

(a) providing a crystal holder containing at least a crystal;

(b) providing a tool capable of retrieving the crystal holder, the tool movable by means of a robot;

(c) providing a positioning device for mounting the crystal holder so that the crystal is in the path of a beam of X-rays; and (d) activating the robot so that the tool retrieves the crystal holder, transfers the retrieved crystal holder to the positioning device, and mounts the transferred crystal holder on the positioning device.

In another aspect, this invention provides a method for aligning a sample comprising a crystal for X-ray crystallographic analysis, which sample is mounted on a positioning device. The method comprises the steps of:

(a) providing a sample, the sample mounted on a positioning device;

(b) providing an apparatus capable of viewing the mounted sample, whereby the apparatus is capable of imaging said mounted sample and determining coordinates of the sample relative to a reference position;

(c) providing a source of power for adjusting the positioning device linearly along three orthogonal axes and rotationally about one of the three axes; and (d) activating the source of power to cause the positioning device to be adjusted such that the sample is positioned into the path of a beam of X-rays, the adjustments of the positioning device being at a plurality of angles, such that the sample is positioned within the beam of X-rays at any angle of rotational adjustment.

In still another aspect, this invention provides a method for determining the structure of a sample containing a crystal by means of X-ray crystallography, which method comprises the steps of:

(a) providing a crystal holder containing at least a crystal;

(b) providing a tool capable of retrieving the crystal holder, the tool movable by means of a robot;

(c) providing a positioning device for mounting the crystal holder so that the crystal is in the path of a beam of X-rays;

(d) activating the robot so that the tool retrieves the crystal holder, transfers the retrieved crystal holder to the positioning device, and mounts the transferred crystal holder on the positioning device;

(e) providing an apparatus capable of viewing the mounted sample, whereby the apparatus is capable of imaging said mounted sample and determining coordinates of the sample relative to a reference position;

(f) providing a source of power for adjusting the positioning device linearly along three orthogonal axes and rotationally about one of the three axes;

(g) activating the source of power to cause the positioning device to be adjusted such that the sample is positioned into the path of a beam of X-rays, the adjustment of the positioning device being at a plurality of angles, such that the sample is positioned within the beam of X-rays at any angle of rotational adjustment;

(h) providing a beam of X-rays, the beam aimed at the sample; and (i) recording scattering of X-rays from the sample.

In still another aspect, this invention provides a device for holding a crystal comprising:

(a) a base;

(b) an attachment element projecting from the base;

(c) a stem projecting from the attachment element, the stem supporting a loop for holding the crystal; and (d) at least one aperture in the attachment element for allowing venting of the device, the device capable of being attached to both a storage cell and a positioning device.

In still another aspect, this invention provides an apparatus for retrieving a crystal holder from a storage cell comprising:

(a) a rotatable element capable of retrieving the crystal holder from the storage cell;

(b) a means for rotating a rotatable element in a given direction of rotation when the rotating means is in a locked mode;

(c) a means for providing a controlled amount of torque when the rotating means is slipping relative to the rotatable element; and (d) a means for activating the rotating means and the torque controlling means.

In a preferred embodiment, an apparatus for retrieving the crystal holder from the storage cell comprises:

(a) a clutch having a cylindrical housing, the housing comprising a bore surrounded by a wall;

(b) a cylindrical plunger capable of moving axially within the bore of the housing;

(c) the plunger having at least one elongated grove on the exterior periphery thereof, the groove capable of receiving a locking pin;

(d) the housing having at least one aperture extending through the wall thereof;

(e) at least one spring pin retained in the aperture, the pin capable of engaging the elongated groove when the plunger is disposed in a first position in the housing, the pin capable of disengaging the elongated groove when the plunger is disposed in a second position in the housing;

(f) a means in the housing for resiliently biasing the plunger toward the first position in the housing;

(g) a friction plate in contact with the interior wall of the housing, the friction plate providing friction between an output flange and the friction plate; and (h) a shaft attached to the plunger, the shaft capable of transmitting torque to the friction plate, the shaft further capable of moving axially with respect to the friction plate.

In still another aspect, this invention provides a device for holding a plurality of samples, the device comprising a plurality of storage cells. The device is capable of maintaining the temperature of the samples at a temperature of not greater than about 160° K. Each of the storage cells has a guided passageway; the guided passageway has a base at the lower end thereof and an opening at the upper end thereof. The area of the opening is greater than the area of the base. At least one side-wall circumscribes the base and the opening. The base is of sufficient area to allow placement of a sample holder. The opening is of sufficient area to allow ingress of a tool for retrieving the sample holder. The base has attached thereto a means for locking the sample holder to the sample-holding device. The device may also be equipped with a lid that can be moved by means of a robot.

This invention also provides various tools and auxiliary devices for carrying out the methods described herein.

This invention provides numerous advantages over conventional methods of X-ray crystallography. First, this invention makes it possible to reduce the number of trained operators required to conduct X-ray analysis of crystals. Second, this invention makes it possible to analyze crystals without the need for an operator to be present. Third, this invention makes it possible to increase the speed of analysis by X-ray crystallography, thereby increasing the throughout of the analysis. Fourth, this invention makes it possible to standardize the handling of samples and reduce the possibility of errors by the operator. This invention also facilitates collection of data 24 hours per day, seven days per week, thereby increasing the utilization of expensive X-ray crystallography equipment. This invention further facilitates the retrieval and preservation of crystal samples after data has been collected, thereby making it possible to reanalyze the sample at a later date.

DETAILED DESCRIPTION

As used herein, the term "robot" means a machine or device that works automatically or by remote control. As used herein, the term "crystal" means an ordered array of molecules that is capable of diffracting X-rays. As used herein, the term "sample" refers to the crystal contained in the loop of the device for holding a crystal.

Figure 1:
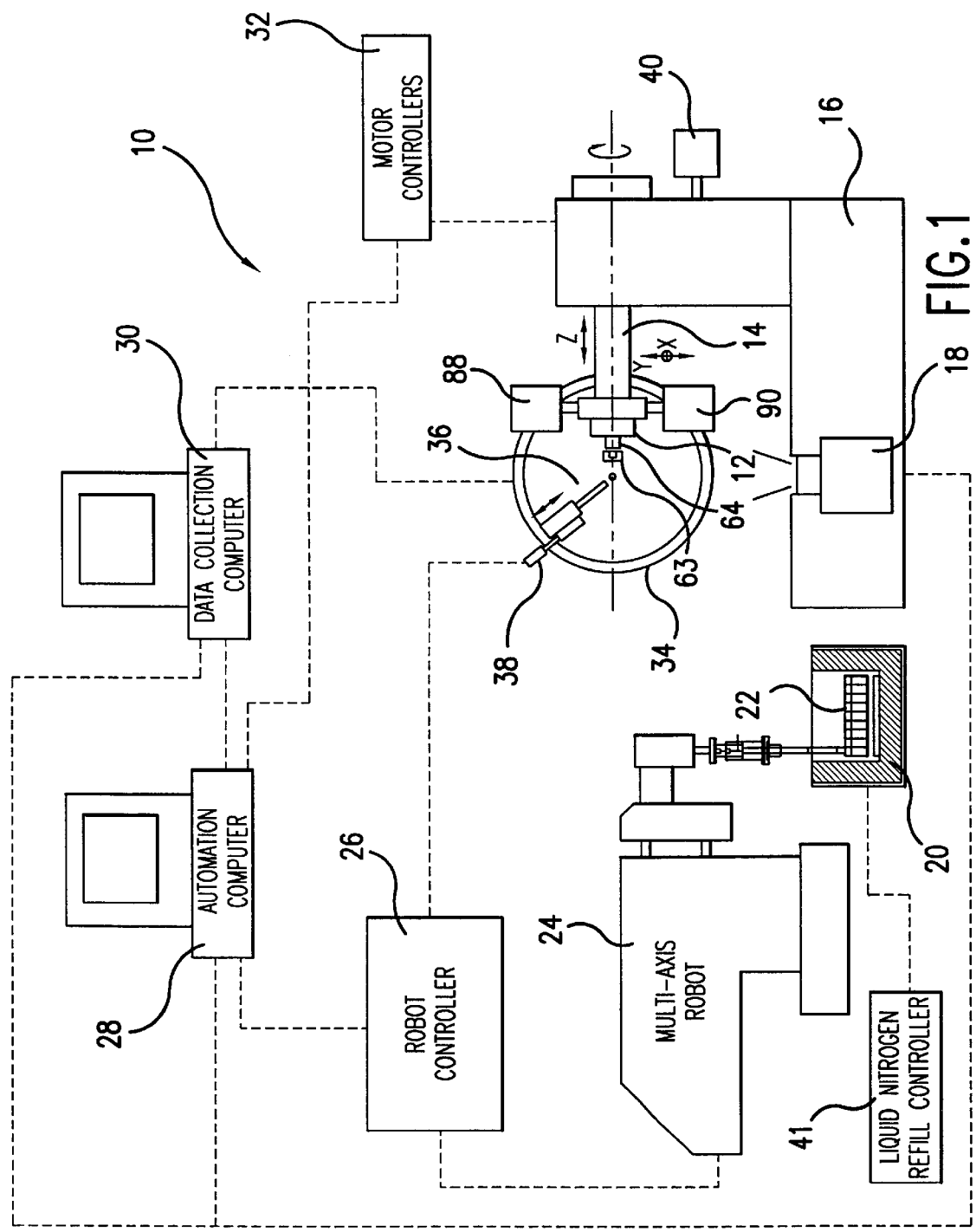
FIG. 1 is a schematic diagram depicting a system for performing the method of this invention.
Figure 2:
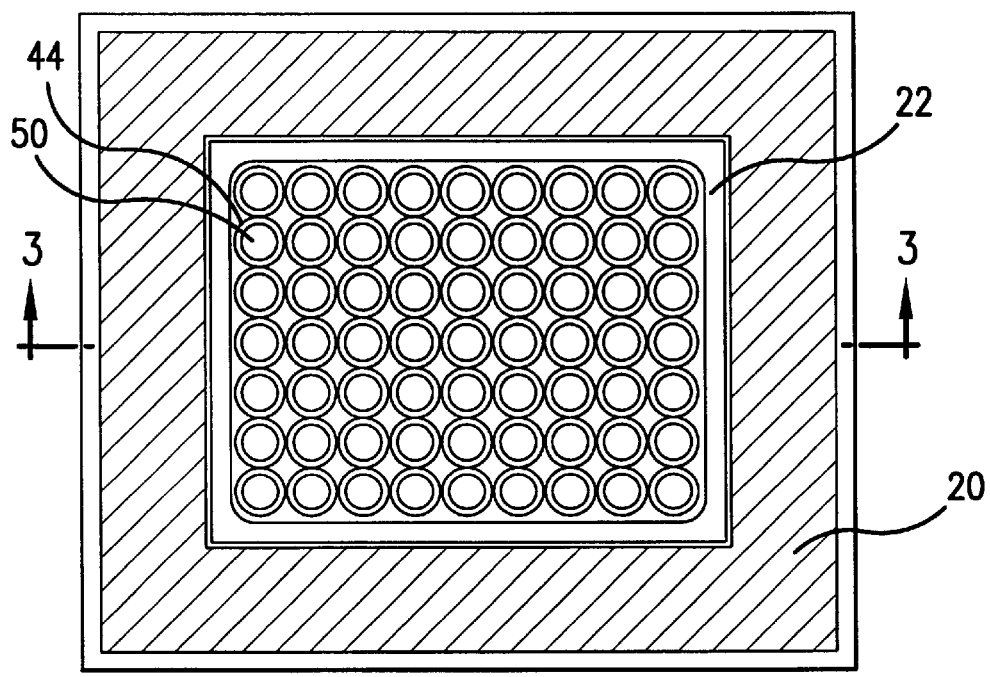
FIG. 2 is a plan view of a sample rack of this invention.
Figure 3:
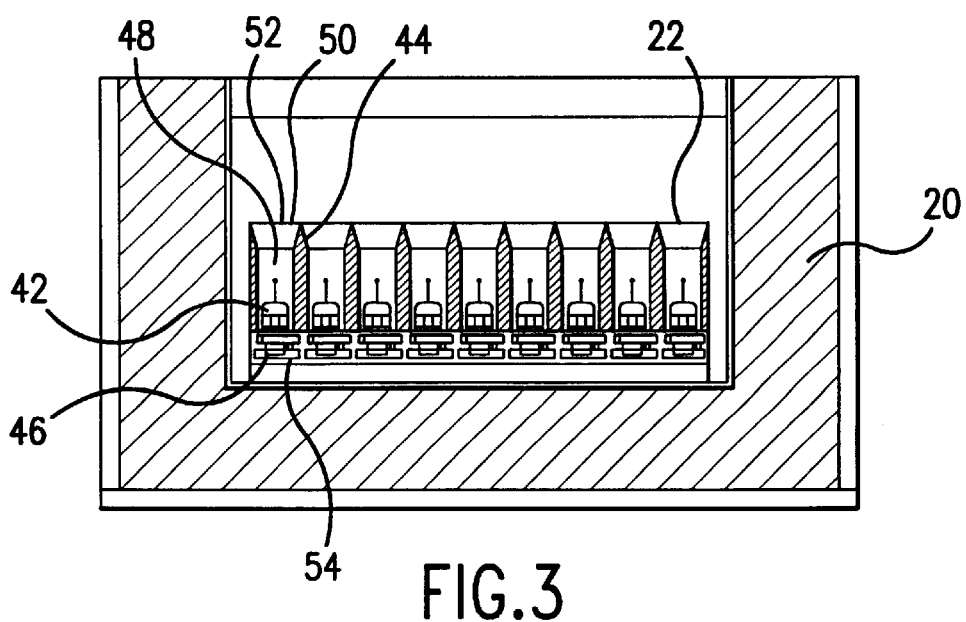
FIG. 3 is a view in cross-section taken along line 3—3 of the sample rack of FIG. 2.
Figure 4:
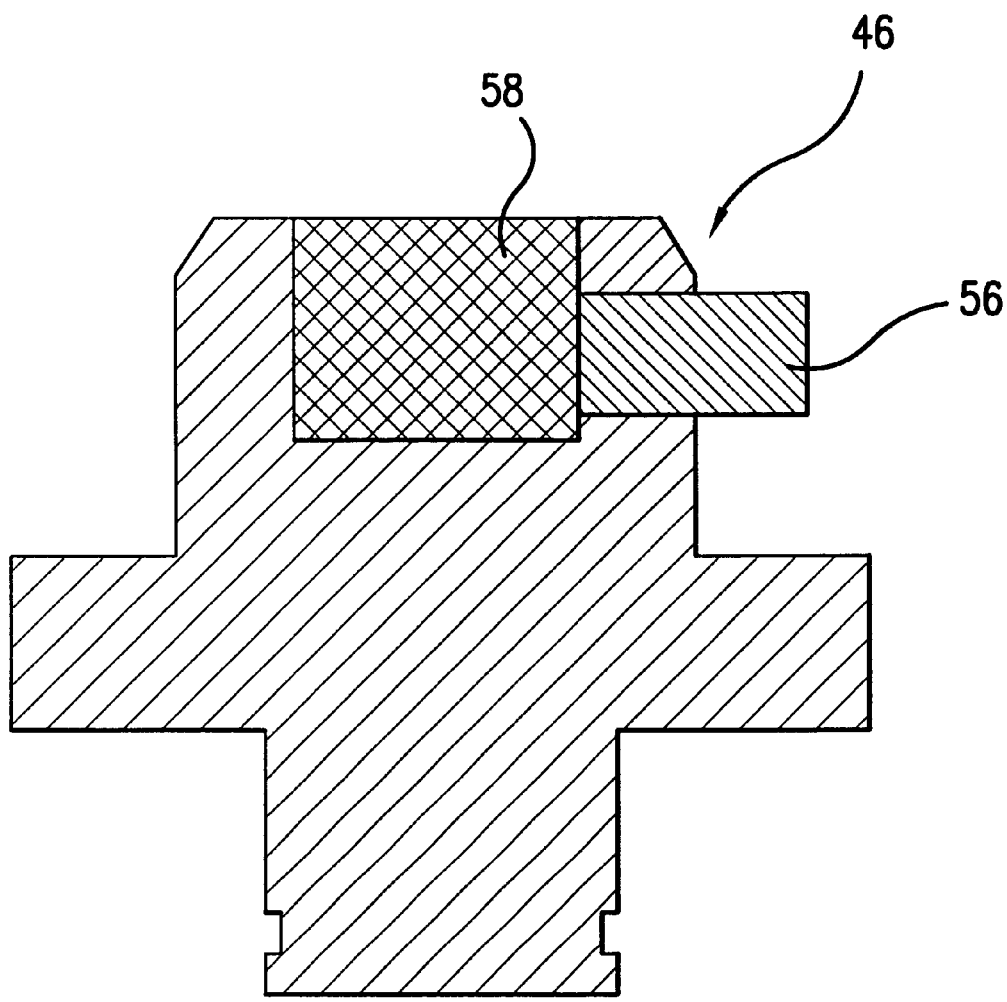
FIG. 4 is a view in cross-section of a magnetic base at the lower end of a storage cell to which can be attached a crystal holder.
Figure 5:
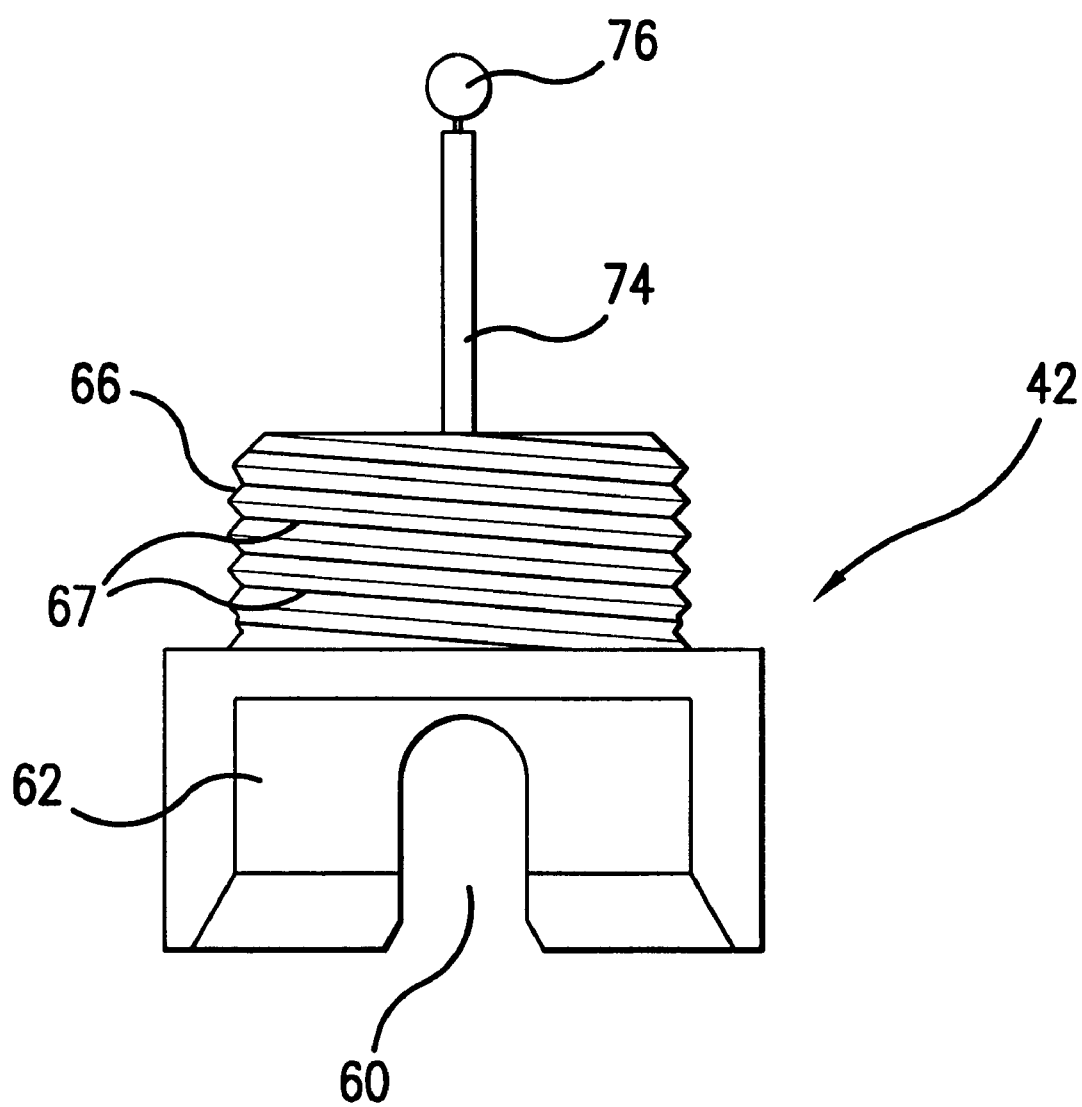
FIG. 5 is a side view in elevation of a crystal holder.
Figure 6:
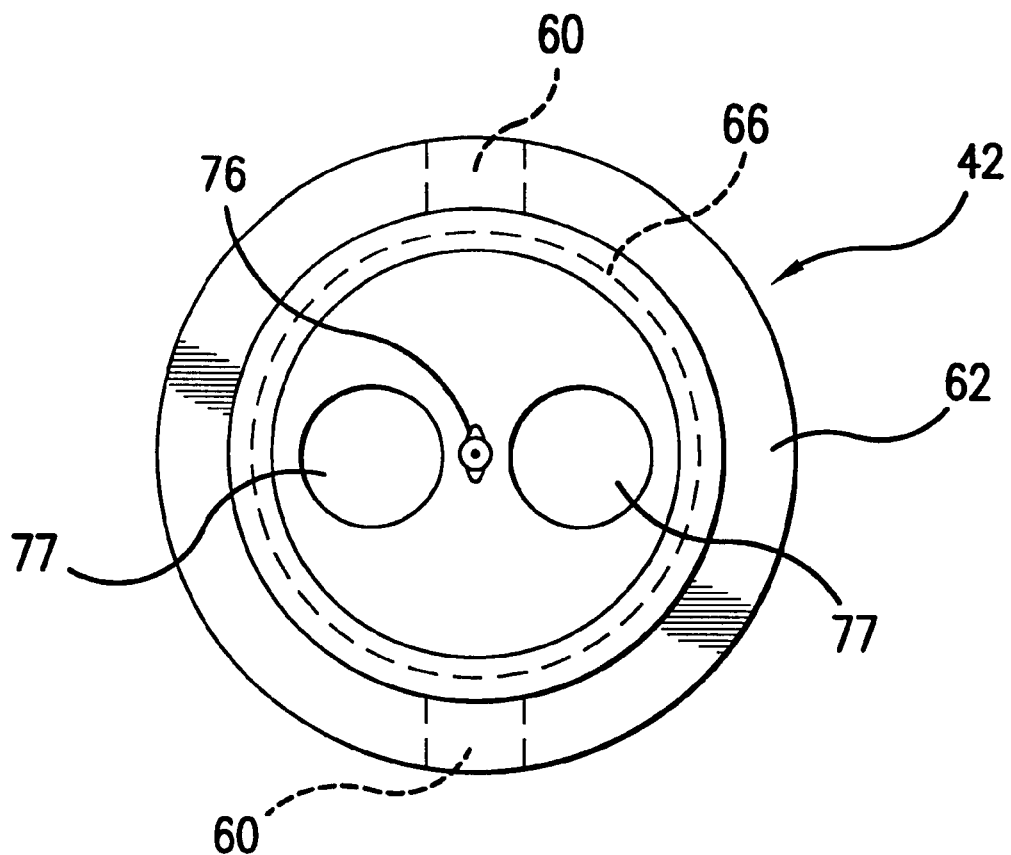
FIG. 6 is a top plan view of a crystal holder.

Referring now to FIG. 1, a system 10 for carrying out the method of this invention comprises an X-ray generator (not shown), a positioning device, such as, for example, a goniometer, 12 mounted on a rotating spindle 14, an instrument base 16, a CCD camera 18, an insulated container 20, a sample rack 22, a multi-axis robot 24, a controller 26 for the robot 24, an automation computer 28, a data collection computer 30, at least one motor controller 32, a detector 34, a cold stream nozzle 36, a cold stream actuator 38, and a motor 40 for translating the spindle 14 along its major axis. Although the computers 28 and 30 are shown as individual components, they can be combined into a single unit. The system 10 preferably also includes an automatic system 41 for replenishing liquid nitrogen to the insulated container 20. Such replenishing systems are well-known to those skilled in the art of X-ray crystallography. An overview of the components for diffractometer systems for X-ray crystallography can be found in *Kirk-Othmer Encyclopedia of Chemical Technology*, Fourth Edition, Volume 25, John Wiley & Sons (New York: 1998), pages 742–759, incorporated herein by reference. The foregoing article describes various components, such as X-ray tubes, detectors, goniometers, and other components typically associated with X-ray crystallography.

Referring now to FIGS. 2, 3, 4, 5, and 6, an insulated container 20 filled with liquid nitrogen is positioned near the X-ray generator. A sample rack 22 holding one or more crystal samples is mounted in the insulated container 20 so that the samples are immersed in liquid nitrogen. The sample rack 22 is used to store crystal samples after the crystal samples have been mounted onto a crystal holder 42. The sample rack 22 is designed to maintain the samples under a layer of liquid nitrogen, which is preferably at a temperature of not greater than about 160° K. The sample rack 22 is constructed to render insertion and removal of crystal holders 42 by either a human operator or the robot 24 more efficient. The sample rack 22 comprises an array of storage cells 44, each storage cell 44 capable of holding one crystal holder 42. Each storage cell 44 comprises a magnetic base 46 and a guided passageway 48 leading from an opening 50 in the storage cell 44 at the upper end 52 of the storage cell 44 to the magnetic base 46 at the lower end 54 of the storage cell 44. The guided passageway 48 is circumscribed by a wall 55 running from the upper end 52 of the storage cell 44 to the lower end 54 of the storage cell 44. The sample rack is preferably constructed of a metal. It is also possible to equip the sample rack with a lid (not shown). This optional lid can be moved by means of a robot to allow access to the crystals holder 42 in the storage cells 44.

The guided passageway 48 is preferably constructed such that the opening 50 at the upper end 52 of the storage cell 44 has a greater area than the base 46 at the lower end 54 of the storage cell 44. This type of construction makes it easy to introduce the crystal holder 42 into the storage cell 44.

The purpose of the magnetic base 46 is to retain the crystal holder 42 at the lower end 54 of the storage cell 44 by magnetic attraction once the crystal holder 42 has been inserted into the storage cell 44 by the robot 24 or the human operator. The crystal holder 42 is preferably made of a material that is magnetically attracted to a ferromagnetic material. A pin 56 extending radially outward from a ferromagnetic material 58 of the magnetic base 46 engages a notch 60 in the base 62 of the crystal holder 42 to prevent relative rotation between the crystal holder 42 and the magnetic base 46. The guided passageway 48 guides the movement of the human operator or the robot 24 when the crystal holder 42 is inserted into the storage cell 44. In addition, the guided passageway 48 protects neighboring samples from damage when a human operator is inserting or removing a crystal holder 42. This feature is especially important in the case of a human operator, because visibility is limited when the sample rack 22 is filled with liquid nitrogen.

The crystal holders 42 are preferably fabricated from a ferromagnetic material, such as, for example, steel. The use of a ferromagnetic material allows secure attachment of the crystal holder 42 to the magnetic mount 63 that is attached to the end 64 of the positioning device 12 and the magnetic base 46 of the storage cell 44 in the sample rack 22. An attachment element 66 of the crystal holder 42 projects from the base 62 of the crystal holder 42. The attachment element 66 is threaded with a standard male screw thread 67. The attachment element 66 can be attached to a mating female screw thread 68 incorporated into an end 70 of a robot tool 72. Such a screw means of attachment is preferred, because it provides an efficient retrieval method for the samples when they are immersed in liquid nitrogen. Projecting from the attachment element 66 of the crystal holder 42 is a stem 74, at the end of which is located a loop 76 for holding the crystal sample. The attachment element 66 preferably has an aperture 77 formed therein to allow liquid nitrogen to flow through the crystal holder 42.

Figure 7:
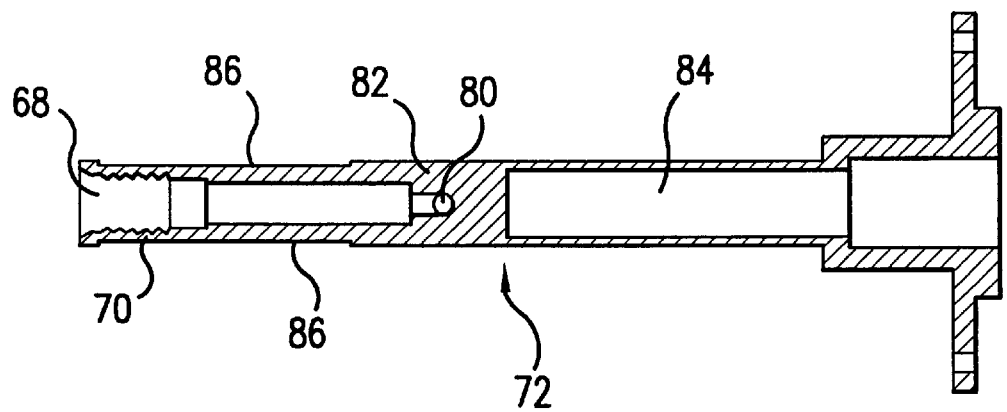
FIG. 7 is a schematic diagram in cross-section of a robot tool for retrieving a crystal holder.
Figure 8:
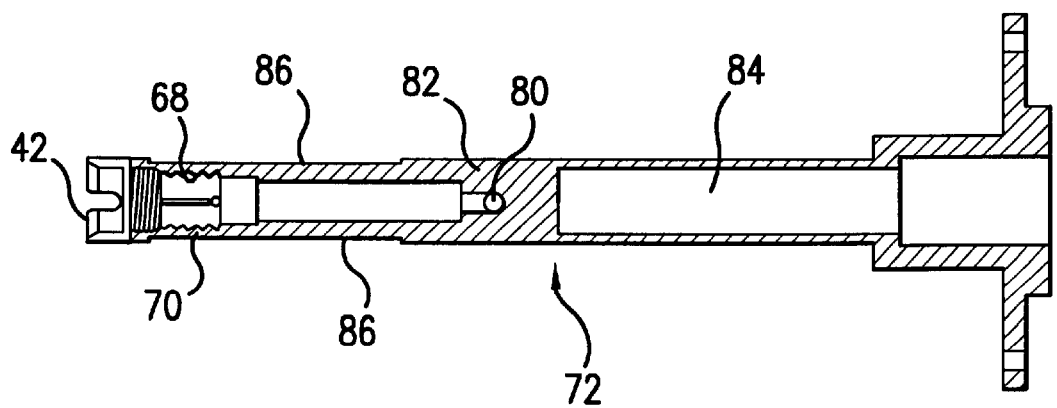
FIG. 8 is a schematic diagram in cross-section of a robot tool having a crystal holder attached thereto.
Figure 9:
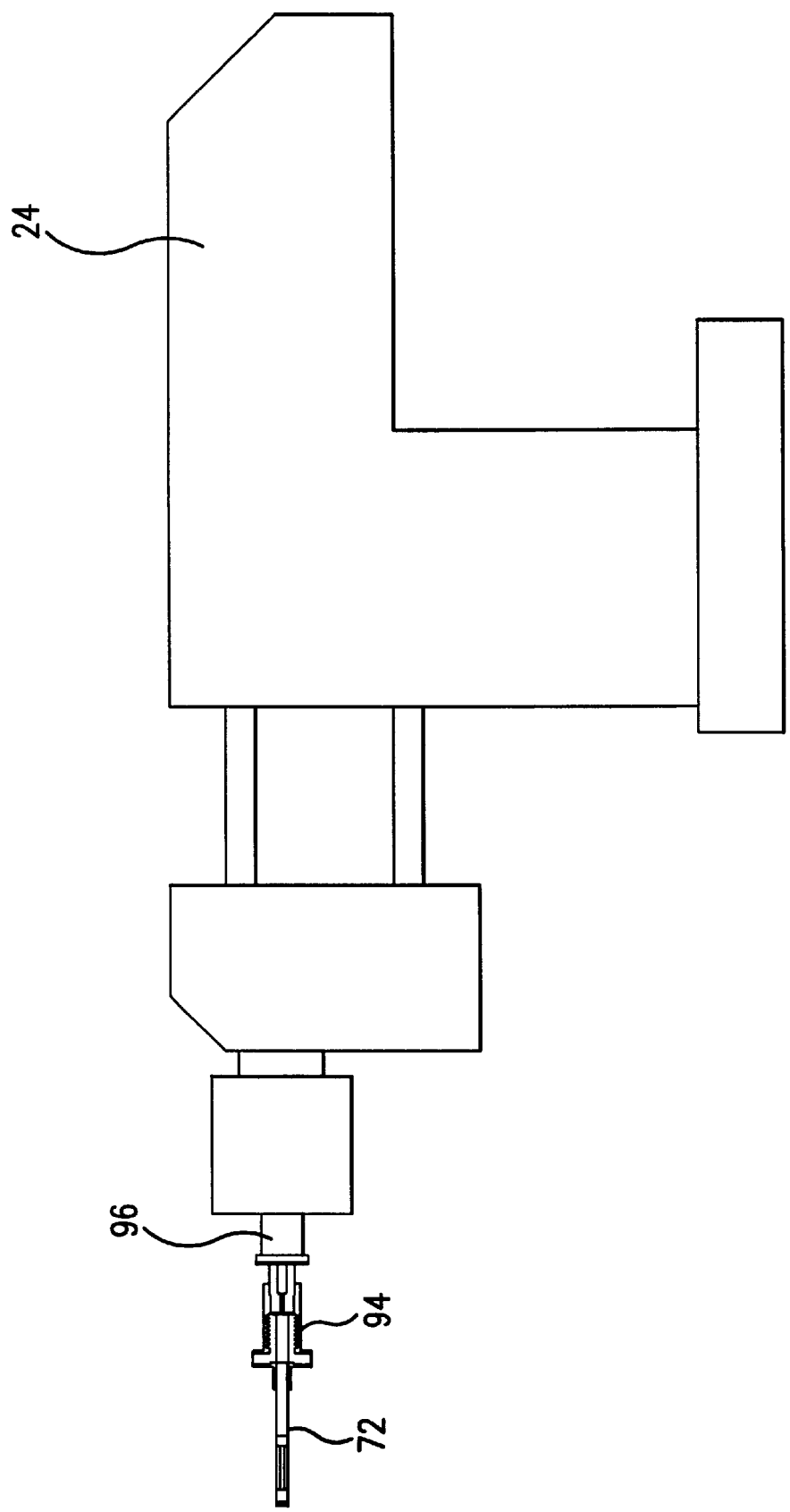
FIG. 9 is a schematic diagram of a robot tool, clutch, robot, and crystal holder.

The multi-axis robot 24 is mounted near the insulated container 20 and within reach of the positioning device 12. Referring now to FIGS. 7 and 8, the robot 24 has an extension referred to herein as the robot tool 72, which contains a female screw thread 68 for mating with the male screw thread 67 of a crystal holder 42. The robot tool 72 is capable of retrieving the crystal holder 42, which contains the sample, from the sample rack 22 and inserting the crystal holder 42 onto the positioning device 12 for data collection. The robot tool is also capable of retrieving the crystal holder 42 from the positioning device 12 and inserting the crystal holder 42 into the sample rack 22 for storage. The robot tool 72 is designed to maintain the sample at a cryogenic temperature, near to that of liquid nitrogen, i. e., a temperature not in excess of about 160° K., during the short time that the sample is in transit. The robot tool 72 is also designed to shield the sample from ambient air when the crystal holder 42 is united with the robot tool 72. The robot 24 is able to retrieve the crystal holder 42 by contacting the crystal holder 42 with the end 70 of the robot tool 72 and rotating the robot tool 72 clockwise so that the crystal holder 42 and the robot tool 72 are screwed together.

Before being used to grasp the crystal holder 42, the robot tool 72 is immersed in liquid nitrogen for a short period of time (typically 20 seconds) in order to cool the robot tool 72 to a temperature near to that of liquid nitrogen. Vent apertures 80 in the body 82 of the robot tool 72 allow air to escape the interior cavity 84 of the robot tool 72 as liquid nitrogen fills the interior cavity 84 of the robot tool 72. When the robot tool 72 and the crystal holder 42 are joined, the crystal sample is maintained at a low temperature by the liquid nitrogen inside the interior cavity 84 and by the cold metal walls 86 surrounding the interior cavity 84 of the robot tool 72. Liquid nitrogen flows through the aperture 77 in the crystal holder 42 into the interior cavity 84 of the robot tool 72 when the robot tool 72 and the crystal holder 42 attached thereto are immersed in liquid nitrogen.

The positioning device 12, which is translatable along an X-axis and a Y-axis via stepper motors 88 and 90, respectively, is mounted onto a rotating spindle 14 on the X-ray diffraction instrument. The positioning device 12 is also translatable along a Z-axis by means of a stepper motor 40. Home position sensors (not shown) are built into the X-axis, Y-axis, and Z-axis translations so that a reference position can be found at any time. The stepper motors and the home sensors for the X-axis, Y-axis, and Z-axis translations are connected to a motor controller 32, which in turn communicates with an automation computer 28. Rotation of the spindle 14 is controlled in a similar manner by commands communicated by the automation computer 28. Motions of the multi-axis robot 24 are controlled by the robot controller 26, which also communicates with the automation computer 28. Video output from the CCD camera 18 is input into a frame grabber video card (not shown), which is connected with the automation computer 28. A communication connection is provided between the automation computer 28 and a separate data collection computer 30. Operation of the automated system is described below.

Operation

The operation of this invention involves retrieving samples, contained in crystal holders, from a storage area, mounting the retrieved samples on a positioning device, aligning the mounted samples prior to collecting data, collecting data, and returning the sample to the storage area.

An operator "enters" the identification numbers of the samples that are to be analyzed and initiates the automated process by entering an appropriate command into the data collection computer 30. After this point, no operator intervention is required.

A stored program within the robot controller 26 is activated and the robot 24 retrieves a sample from the sample rack 22 located in the insulated container 20. The robot tool 72 enables the robot 24 to grip the sample while the sample is immersed in liquid nitrogen. The sample is then withdrawn from the sample rack 22 and immediately installed on the magnetic mount 63 on the end 64 of the positioning device 12.

Figure 10:
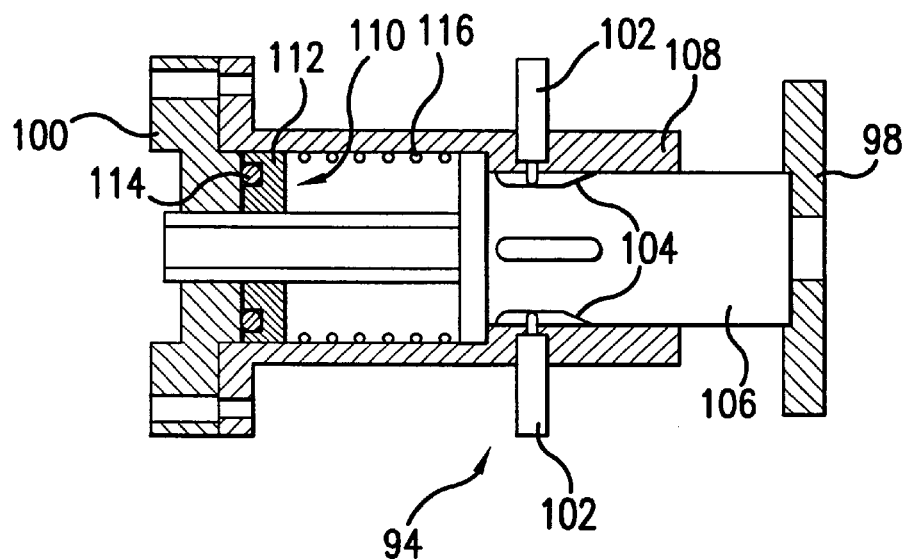
FIG. 10 is a schematic diagram in cross-section of a clutch assembly for transmitting torque to the robot tool. In this figure, the clutch is in a locked mode.
Figure 11:
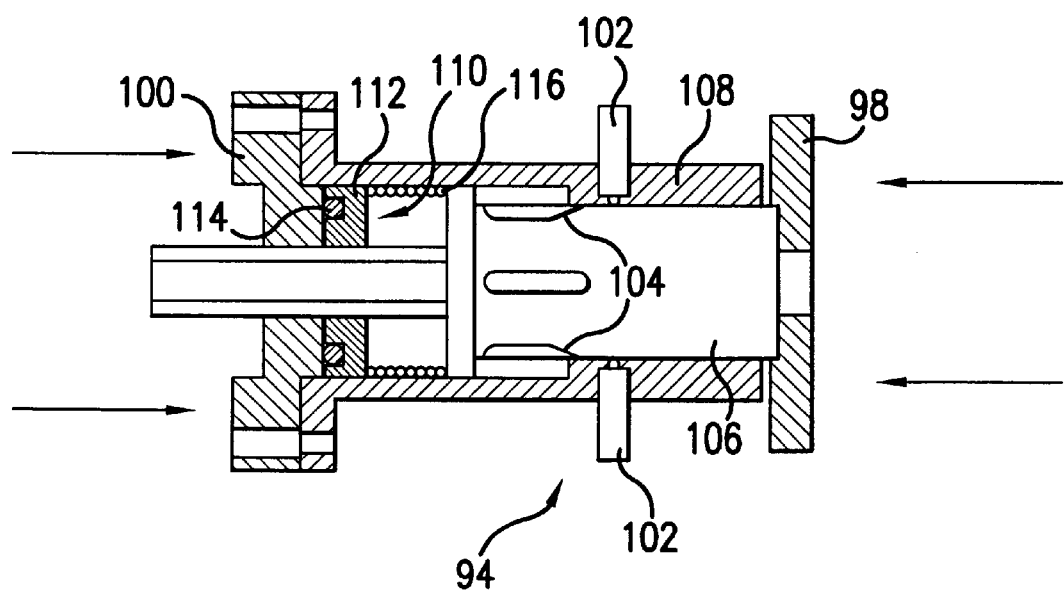
FIG. 11 is a schematic diagram in cross-section of a clutch assembly for transmitting torque to the robot tool. In this figure, the clutch is in a slipping mode.

In order for the robot tool 72 to reliably grasp and release the sample, which is disposed in the crystal holder 42, a clutch 94 connected between the rotation stage 96 of the robot 24 and the robot tool 72 is used. The clutch 94 is illustrated in detail in FIGS. 10 and 11. In general, the clutch can have any of numerous configurations, but, at minimum, in a generic sense, the clutch 94 comprises:

(a) a rotatable element capable of retrieving the crystal holder from the storage cell;
(b) a means for rotating the rotatable element in a given direction of rotation when the rotating means is in a locked mode;
(c) a means for providing a controlled amount of torque when the rotating means is in a slipping mode relative to the rotatable element; and
(d) a means for activating the rotating means and the torque controlling means.

The clutch 94 is normally in the locked mode. When the clutch 94 is in the locked mode, rotation initiated at an input flange 98 is directly transmitted to an output flange 100 without allowing rotational slippage Spring pins 102 protrude into axial grooves 104 in a plunger 106, which is disposed in the bore of a housing 108, thereby preventing rotation of the plunger 106 in the housing 108. Preferably, the plunger 106 and the housing 108 are cylindrical in shape. When the clutch 94 is in the locked mode, any amount of torque can be transmitted to the robot tool 72, up to the torque limits of the robot 24 itself.

To switch the clutch 94 to the slipping mode, an axial force must be imposed on the clutch 94 so that the plunger 106 is shifted relative to the housing 108, typically by approximately 0.2 inches to the left. When the plunger 106 is shifted, the spring pins 102 are disengaged from the grooves 104 in the plunger 106, thereby allowing relative rotation between the plunger 106 and housing 108, and thus between the input flange 98 and the output flange 100. However, when relative rotation occurs, a controlled amount of rotational friction is generated by a friction plate 110, which includes a plate 112 and an o-ring 114, as the friction plate rubs against the output flange 100. A spring 116 resiliently biases the friction plate 110 toward the output flange 100. The level of friction between the friction plate 110 and the output flange 100 can be controlled by appropriate selection of the material and the properties of the o-ring 114 and the spring 116. Materials and properties for the plate 112, o-ring 114, and spring 116 are matters of design choice, and appropriate selection thereof is well-known to those of ordinary skill in the art.

The clutch 94 operates in accordance with the following procedure:

(1) The crystal holder 42, which holds the sample, is seated in the sample rack 22, on the magnetic base 46 of the storage cell 44. The sample rack 22 is immersed in a container 20 of liquid nitrogen.

(2) The robot 24 points the robot tool 72 downwardly and moves to a position above the storage cell 44 in the sample rack 22 near the desired crystal holder 42.

(3) The robot 24 moves the robot tool 72 downwardly until the robot tool 72 just contacts the crystal holder 42. The robot 24 pauses in this position in order to allow the robot tool 72 to cool to a temperature near that of liquid nitrogen. The vent apertures 80 in the robot tool 72 allow the interior cavity 84 of the robot tool 72 to become filled with liquid nitrogen.

(4) The robot 24 moves the robot tool 72 downwardly about 0.25 inch in order to apply axial force to the clutch 94 and to unlock the clutch 94.

(5) Through the use of the rotation stage 96, the robot 24 rotates the robot tool 72 clockwise to screw the crystal holder 42 onto the robot tool 72. The threads 67 of the crystal holder 42 unite with the threads 68 of the robot tool 72. Generally, only approximately one full turn of the robot tool 72 is required to fully screw the crystal holder 42 onto the robot tool 72. Preferably, two additional turns of the robot tool 72 are made to ensure that the crystal holder 42 is fully engaged on the robot tool 72. Because the clutch 94 is unlocked, rotation-wise slippage will occur after the crystal holder 42 becomes fully engaged (i.e., fully screwed on to the robot tool 72). If the clutch 94 were unable to slip, breakage or robot overload would likely occur after full engagement of the crystal holder 42 and the robot tool 72. Axial compliance of the clutch 94, coupled with its ability to slip when unlocked, provides a degree of "forgiveness" in the system. The movements of the robot 24 do not have to match the position or thread length of the crystal holder 42 perfectly. Small errors in robot movements and programming are tolerated because of the axial compliance and slippage of the clutch 94.

(6) After the crystal holder 42 is fully engaged by the robot tool 72, the robot 24 withdraws the robot tool 72 with crystal holder 42 from the sample rack 22 and performs the next operation. The crystal sample on the crystal holder 42 is protected from the warm atmosphere, because it is surrounded by liquid nitrogen inside the interior cavity 84 of the robot tool 72 and protected by the cold metal walls 86 of the robot tool 72 itself.

The robot tool 72 then mounts the crystal holder 42 onto the positioning device 12 in the following manner.

(1) the robot 24 guides the robot tool 72 to a horizontal position (parallel to the base 16) and moves the robot tool 72 to a position near the end 64 of the positioning device 12.

Figure 12:
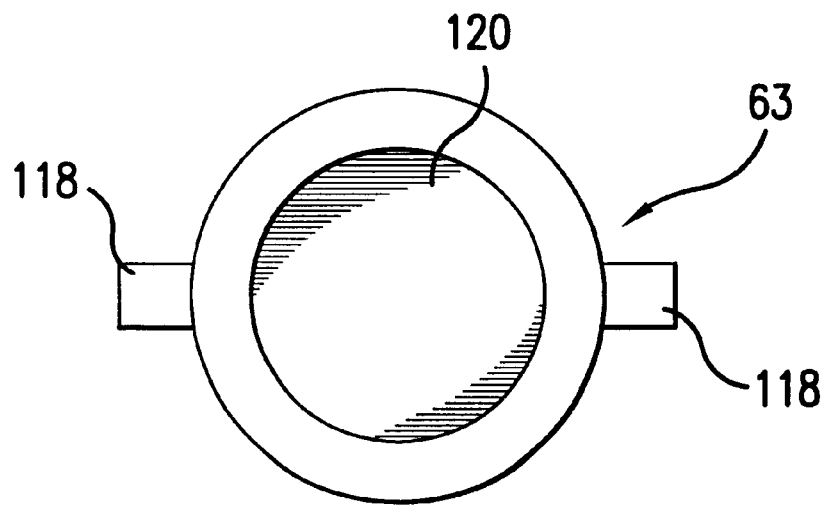
FIG. 12 is a plan view of a magnetic base for the end of the positioning device of the system.
Figure 13:
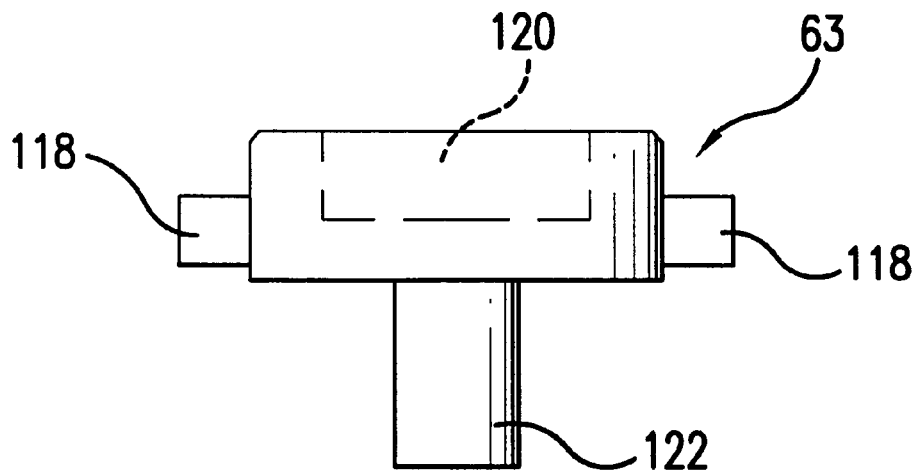
FIG. 13 is a side view in elevation of the magnetic base of FIG. 12.

(2) The robot 24 moves the robot tool 72 toward the magnetic mount 63 until the crystal holder 42 just contacts the magnetic mount 6 at the end 64 of the positioning device 12. The angular position of the crystal holder 42 is such that the notch 60 in the base 62 of the crystal holder 42 engages an alignment pin 118 of the magnetic mount 63. This engagement prevents angular rotation of the crystal holder 42 relative to the magnetic mount 63. As shown in FIGS. 12 and 13, the magnetic mount 63 also includes a magnet, i. e., a ferromagnetic material, 120 and an attachment pin 122. The magnet 120 serves to retain the crystal holder 42 by magnetic attraction after the crystal holder 42 has been mounted onto the magnetic mount 63 on the end 64 of the positioning device 12. The attachment pin 122 serves to attach the magnetic mount 63 to the end 64 of the positioning device 12. At this point, the clutch 94 is locked because it has not been significantly compressed in the axial direction.

(3) The robot 24 rotates the robot tool 72, via the rotation stage 96, in the counter-clockwise direction, preferably two turns, to ensure that the robot tool 72 is completely unscrewed from the crystal holder 42. Because the clutch 94 is locked, sufficient torque can be applied to unscrew the crystal holder 42 from the robot tool 72, even if the crystal holder 42 and the robot tool 72 are stuck or frozen together.

(4) While rotating in the counter-clockwise direction, the robot tool 72 is drawn away from the end 64 of the positioning device 12, thereby leaving the crystal holder 42 adhered to the magnetic mount 63 at the end 64 of the positioning device 12.

Figure 14:
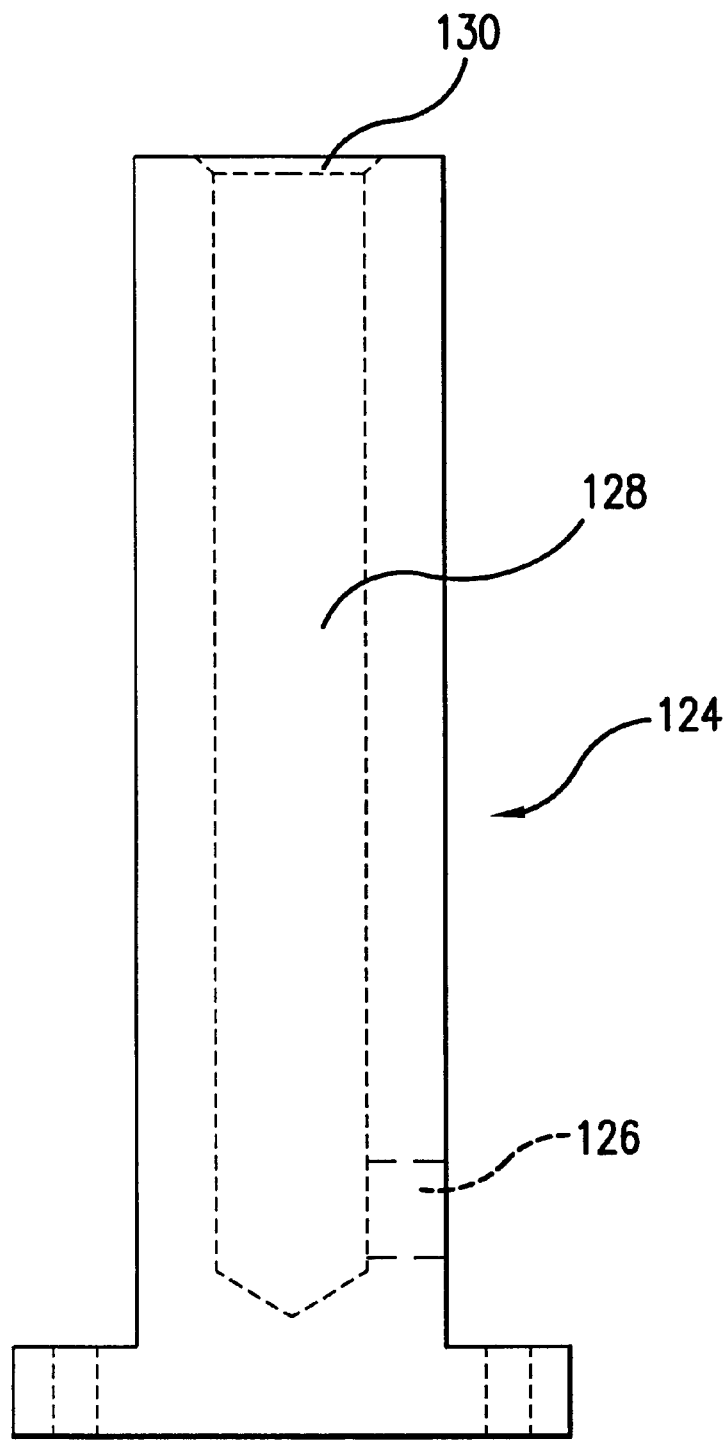
FIG. 14 is a side view in elevation of a dryer for preventing moisture from collecting on the robot tool.

After the crystal holder 42 is mounted onto the positioning device 12, the crystal holder 42 must be properly positioned for data collection. Prior to positioning the crystal holder 42, the robot tool 72 is quickly moved away from the positioning device 12 to a "rest" position in a dryer 124. The dryer 124 is shown in FIG. 14. The purpose of the dryer 124 is to prevent moisture from collecting on the robot tool 72 when the robot tool 72 is not in use. A stream of dry gas, e. g., nitrogen, at ambient temperature, is introduced at port 126, traverses an interior chamber 128, and exits at port 130. The material of construction of the dryer is not critical. When the robot tool 72 is inserted into the interior chamber 128 of the dryer 124, the dry gas prevents moisture from collecting on the robot tool 72.

After being mounted on the positioning device 12, the temperature of the sample is maintained at a low temperature by a cold stream, which is provided through the cold stream nozzle 36, which is positioned as close to the sample as possible. The cold stream nozzle 36 is mounted onto the cold stream actuator 38, so that the cold stream nozzle 36 can be retracted when the crystal holder 42 is mounted onto the positioning device 12 and extended at other times.

At this time, an image processing/sample alignment program is employed to automatically position the sample at the intersection of the X-ray beam and the axis of the spindle. The alignment procedure technique uses a "machine vision"

algorithm to analyze the video information obtained via the CCD camera 18 mounted in the base 16 of the system 10. The alignment procedure repeatedly invokes the machine vision algorithm as described below, and uses the position information obtained to reposition the sample by means of the stepper motors 88, 90, and 40. The cycle described below is repeated until the difference between the actual sample position and the desired sample position is sufficiently small for the purpose of data collection.

The details of a "machine vision" algorithm suitable for this invention will now be discussed. The "machine vision" algorithm can find the centroid and the "tip" (leftmost point in the image) of the crystal sample. In the following discussion, the Z-axis is the axis of rotation of the sample. The $\phi$ angle is the angle of rotation about the Z-axis. The X-axis is the axis horizontal to the instrument base 16 (and CCD camera 18) when the $\phi$ angle is 0°, and the Y-axis is the other orthogonal axis. When the $\phi$ angle is 0°, the vertical direction of the image corresponds to the X-axis while the horizontal direction of the image corresponds to the Z-axis. When the $\phi$ angle is 90°, the vertical direction of the image corresponds to the Y-axis while the horizontal image still corresponds to the Z-axis.

Figure 17:
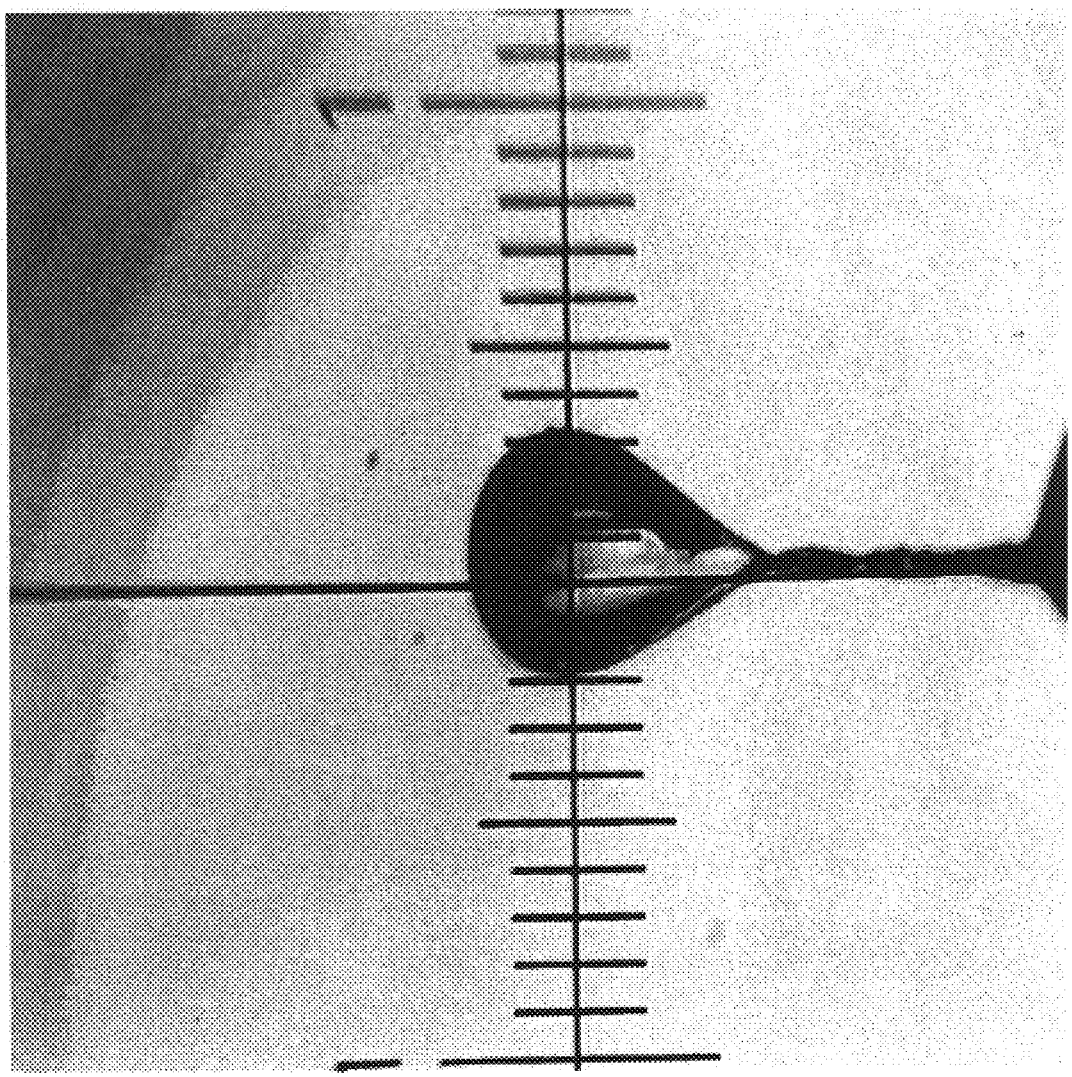
Figure 18:
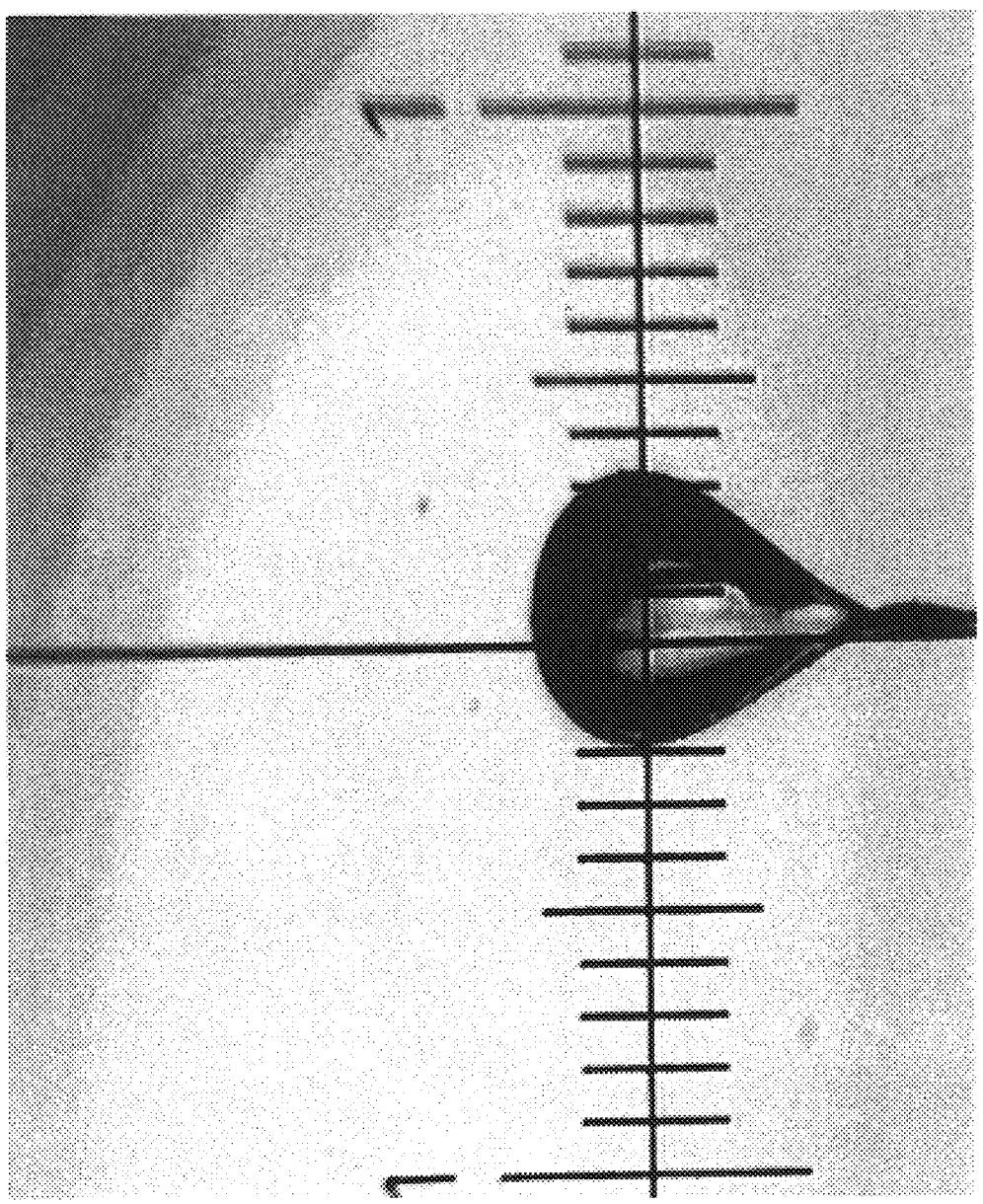

The machine vision algorithm begins with a digitized image, represented as a matrix of eight bit numbers corresponding to the pixels in the image. A typical starting image is shown in FIG. 17. The goal of the image processing method described below is to determine the centroid of the loop 76 of the crystal holder 42 as shown in the center of FIG. 17. The machine vision algorithm must be capable of discriminating between the loop 76 of the crystal holder 42 and the other elements of the image. These elements include the cross-hairs and reticle graduations and the stem 74 of the crystal holder 42. At a minimum, the machine vision algorithm comprises the following steps:

(1) Ignore the "rightmost 10% of the image as shown in FIG. 18

Figure 19:
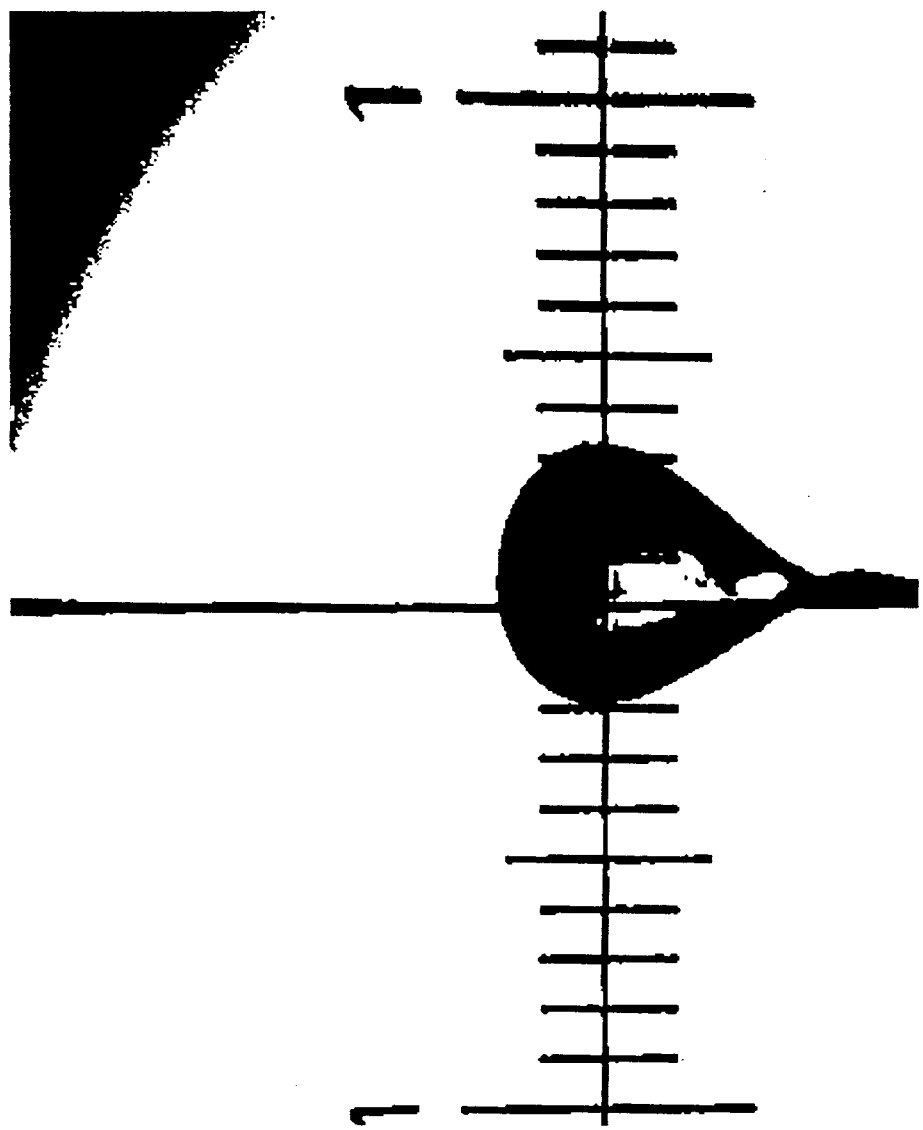

(2) Convert the eight bit grayscale image to two bit black and white image by converting the darkest 12% of the pixels to black and the remaining pixels to white as shown in FIG. 19.

Figure 20:
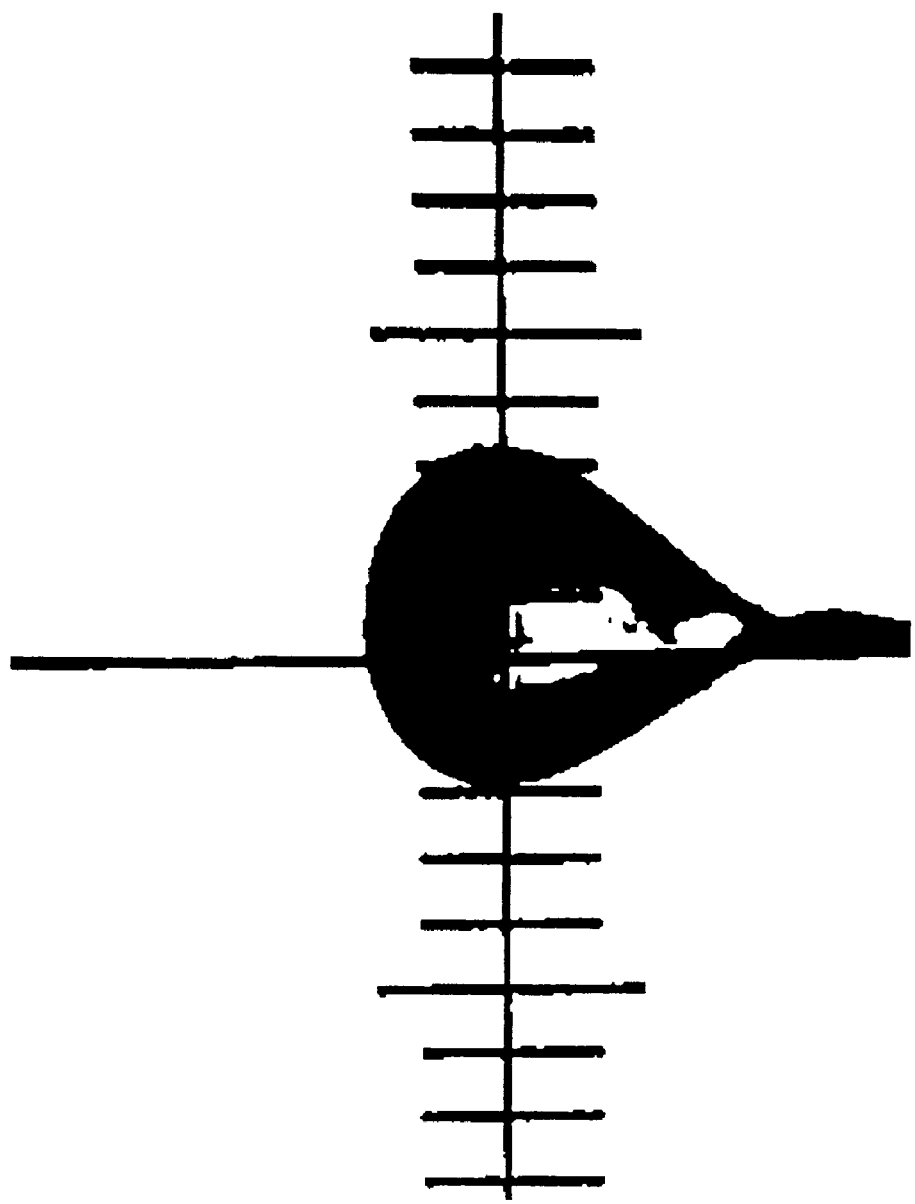

(3) Blank the leftmost 20%, the topmost 10%, and the bottommost 10% of the image, thereby eliminating the effect of the shadow of the cold stream and reducing the influence of non-uniform illumination, as shown in FIG. 20.

Figure 21:
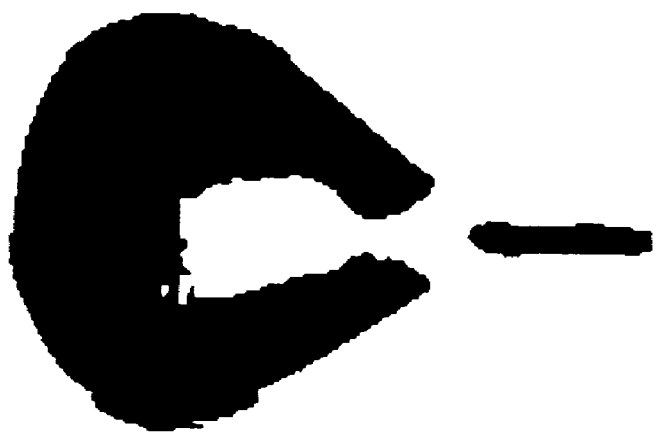

(4) Perform a "thinning" algorithm as follows:
   (a) for each dark pixel, a 20×20 window (with the dark pixel at the center of the window) is examined;
   (b) if fewer than 280 dark pixels are contained in this window, the pixel is changed to white;
   (c) this eliminates grid lines and other artifacts, as shown in FIG. 21.

(5) Calculate the centroid of the remaining black pixels.

Various refinements of the foregoing algorithm have been developed. These refinements utilize techniques known to those skilled in the art. These refinements increase reliability for unusual cases, such as the case of very small crystals.

The alignment procedure consists of two parts—an initial acquisition phase followed by a fine centering phase. In the initial acquisition phase, the sample is moved by the motors along the X-axis and the Z-axis to a starting position. The starting position is defined such that the system will know that the sample is either out of the camera image completely or in the right half of the camera image. It is important to begin in this position so that the stem 74 on which the sample loop 76 is mounted will not confuse the system.

Figure 15:
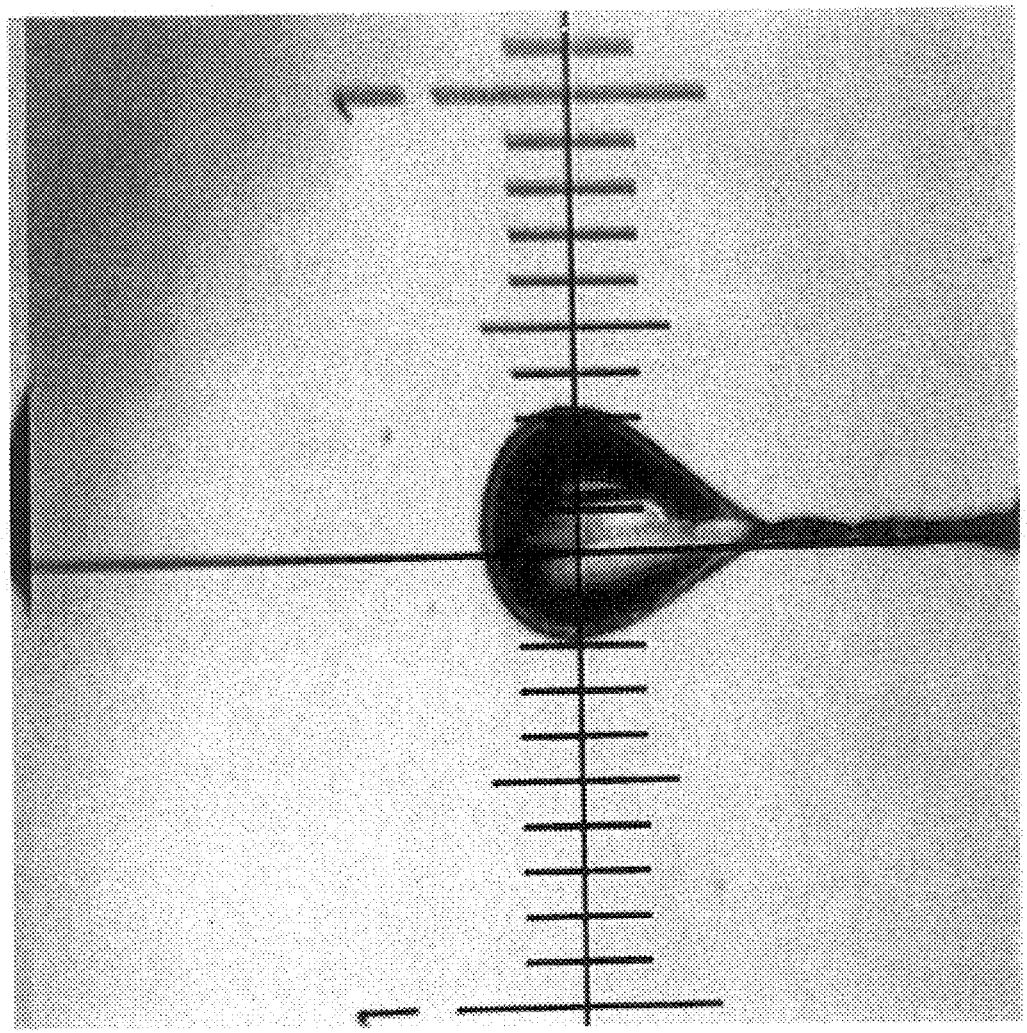
FIGS. 15, 16, 17, 18, 19, 20, and 21 are photographs illustrating the displays of the crystal at various points in the procedure of this invention.
Figure 16:
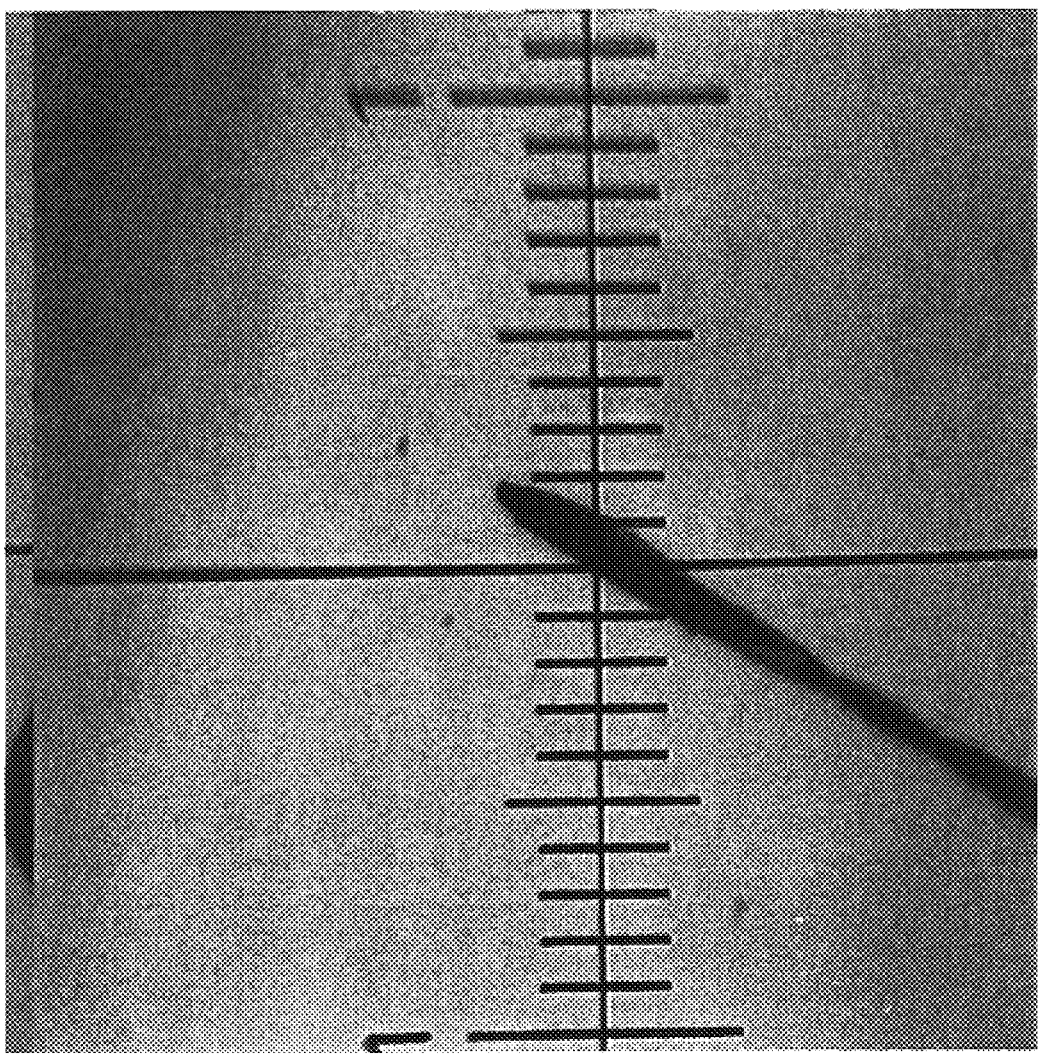

The "machine vision" algorithm is then invoked. If the sample is not found, a search pattern commences. The search pattern involves a zigzag motion of the sample along the X-axis and the Z-axis, invoking the machine vision algorithm at each position in the search pattern. Once the sample is found, the system uses the centroid information obtained from the machine vision algorithm to center the sample to the X-axis and the Z-axis, by means of stepper motors 88 and 40. The centering is then repeated to account for the possibility that the sample was not completely within the field of view of the CCD camera 18. This step completes the initial acquisition phase of the alignment routine. At this point, the position of the sample along the X-axis and the Z-axis should be reasonably close to proper alignment, but the Y-axis will typically be misaligned by a significant amount. In theory, all that should have to be done to complete the alignment is to move the $\phi$ angle to 90° and repeat the centering process. However, there is a potential problem with this technique for some samples. Many crystal samples are very flat. When the face of the crystal is viewed, the "machine vision" algorithm is very accurate (see FIG. 15). However, when the edge of the crystal is viewed, it is difficult to distinguish between the sample, the loop 76, and the stem 74 of the loop 76. An example of this problem can be seen in FIG. 16. Thus, attempting to properly align the sample by using only two angles (0° and 90°) is potentially harmful to accuracy if one of the two angles happens to result in a "machine vision" image similar to that of FIG. 16 or if the sample has some other feature that makes it unusual, thereby confusing the "machine vision" algorithm. To adjust for this possibility, the system uses information at a plurality of angles between 0° and 90°, inclusive, to ascertain the most likely true position of the crystal sample in three dimensions. The algorithm, as currently implemented, is as follows:

(1) Move the $\phi$ angle from 0° to 90° in 5° increments, using the "machine vision" algorithm to find the centroid of the crystal sample at each angle.

(2) Perform a parametric least squares fit to the equation:

$$V_i = \Delta X \cos\phi_i + \Delta Y \sin\phi_i$$

where $V_i$ represents the vertical offset of the centroid of the image of the crystal sample at the angle $\phi_i$, and $\Delta X$ represents the unknown offset of the centroid of the image of the sample from the X-axis and the Y-axis and $\Delta Y$ represents the unknown offset of the centroid of the image of the sample from the Y-axis.

(3) When the values of $\Delta X$ and $\Delta Y$ are found, adjust the motors to center the sample.

(4) Adjust the Z-axis by using a simple average of all of the offsets from the horizontal in the image.

(5) Repeat the above steps (1), (2), (3), and (4) with the exception that the $\phi$ angle is moved from 90° to 0° in 5° increments.

(6) Continue to iterate the foregoing steps (1), (2), (3), (4), and (5) until the closure criteria are met. Currently, the closure condition is one of the following:
   (a) current sum of the squares of the offsets (from the X-axis, the Y-axis, and the Z-axis) is less than 225 pixels squared.
   (b) difference between the current sum of the squares of the offsets and the immediately previous iteration of the sum of the squares of the offsets is less than 225 pixels squared.
   (c) six (6) iterations without fulfilling (a) or (b).

The first condition (a) is considered perfect alignment. The second condition (b) is a case where alignment is no longer being significantly improved, and prevents oscillation between two equally good solutions. The final condition (c) is considered an alignment failure.

(7) When the closure condition is met, alignment success or failure is reported to the data collection computer 30. The data collection computer 30 then commences taking data if the alignment was successful, or requests the next crystal if the alignment failed.

This technique uses information at 19 different angles; thus, it is more robust to errors at a certain angle than an algorithm that uses only two angles.

At this point, a signal is sent to the data collection computer 30 and the X-ray diffraction analysis of the sample is begun.

At the end of the data collection phase, a computer program stored in the robot controller 26 is activated, guiding the robot 24 to retrieve the sample from the positioning device 12 and return it to its original position in the sample rack 22.

The following procedure is employed to return the crystal holder 42 to the sample rack 22.

(1) The robot 24 guides the robot tool 72 to a horizontal position (parallel to the base 16) and moves the robot tool 72 to a position near the end of the crystal holder 42. The crystal holder 42 is still mounted on the magnetic mount 63 on the end 64 of the positioning device 12.

(2) The robot 24 moves the robot tool 72 toward the crystal holder 42 until the robot tool 72 just contacts the crystal holder 42.

(3) The robot 24 moves the robot tool 72 about 0.2 inch toward the positioning device 12 in order to apply axial force to the clutch 94 and to unlock the clutch 94.

(4) By means of the rotation stage 96, the robot 24 rotates the robot tool 72 clock-wise to screw the crystal holder 42 onto the robot tool 72. Generally only about on full turn is required to screw the crystal holder 42 onto the robot tool 72. Preferably, two additional turns are made to ensure that the crystal holder 42 is fully engaged on the robot tool 72.

(5) After the crystal holder 42 is fully engaged on the robot tool 72, the robot 24 withdraws the robot tool and the crystal holder 42 from the magnetic mount 63.

(6) The robot 24 points the robot tool 72 downwardly and moves to a desired position above the appropriate storage cell 44 in the sample rack 22.

(7) The robot 24 moves robot tool 72 downwardly until the crystal holder 42 just contacts the magnetic base 46 at the bottom of the storage cell 44. The angular position of the crystal holder 42 is such that the notch 60 in the base 62 of the crystal holder 42 engages the pin 56 in the magnetic base 46. This engagement prevents angular rotation of the crystal holder 42 relative to the magnetic base 46. At this point, the clutch 94 is locked because it has not been significantly compressed in the axial direction.

(8) The robot 24 rotates the robot tool 72 two turns in the counter-clockwise direction to ensure that the crystal holder 42 is fully unscrewed from the robot tool 72. Because the clutch 94 is locked, sufficient torque can be applied to unscrew the parts, even if the crystal holder 42 and the robot tool 72 are stuck or frozen together.

(9) While continuing to rotate in the counter-clockwise direction, the robot tool 72 is withdrawn from the storage cell 44 in the sample rack 22, leaving the crystal holder 42 adhered to the magnetic base 46 at the bottom of the storage cell 44.

The entire operation process is then repeated for the next sample to be analyzed. After all of the selected samples have been analyzed and returned to their positions in the sample rack 22, the robot tool 72 is parked in a rest position and the system is placed in a standby mode.

Various modifications and alterations of this invention will become apparent to those skilled in the art without departing from the scope and spirit of this invention, and it should be understood that this invention is not to be unduly limited to the illustrative embodiments set forth herein.

What is claimed is:

1. A method for mounting a sample comprising a crystal, said method comprising the steps of:

(a) providing a crystal holder containing at least one crystal;

(b) providing a tool capable of retrieving said crystal holder, said tool movable by means of a robot;

(c) providing a positioning device for mounting said crystal holder so that said crystal is in the path of a beam of X-rays; and (d) activating said robot so that said tool retrieves said crystal holder, receives a sufficient amount of a fluid to maintain said crystal in said crystal holder at a temperature not in excess of about 160° K., transfers said retrieved crystal holder to said positioning device, and mounts said transferred crystal holder on said positioning device, whereby said crystal in said retrieved crystal holder is maintained at a temperature not in excess of about 160° K.

2. The method of claim 1, wherein said crystal holder is mounted to said positioning device by means of screw threads.

3. The method of claim 1, wherein said crystal in said retrieved crystal holder is shielded from air.

4. The method of claim 1, wherein said fluid is liquid nitrogen.

5. The method of claim 1, wherein said fluid is nitrogen that has been cooled to a temperature not in excess of about 160° K.

6. The method of claim 1, wherein said tool shields said sample from ambient air when said crystal holder is united with said tool.

* * * * *